United States Patent [19]

Miki et al.

[11] Patent Number: 4,983,441

[45] Date of Patent: Jan. 8, 1991

[54] DEODORANT COMPOSITION AND DEODORANT COMPOSITE MATERIAL

[75] Inventors: Yoshiaki Miki, Yokohama; Tsunehisa Ueda, Zushi; Tadao Natsuume, Yokosuka, all of Japan

[73] Assignee: Nippon Zeon Co., Ltd., Tokyo, Japan

[21] Appl. No.: 397,512

[22] Filed: Aug. 23, 1989

Related U.S. Application Data

[62] Division of Ser. No. 118,884, Nov. 10, 1987, Pat. No. 4,906,462.

[30] Foreign Application Priority Data

| Nov. 14, 1986 | [JP] | Japan | 61-271224 |
| Jun. 30, 1987 | [JP] | Japan | 62-161195 |
| Aug. 6, 1987 | [JP] | Japan | 62-196641 |

[51] Int. Cl.$^5$ .............................................. B32B 9/00
[52] U.S. Cl. ...................................... 428/65; 424/486; 424/76.21
[58] Field of Search ........................... 424/65, 76, 486

[56] References Cited

U.S. PATENT DOCUMENTS

| 2,856,330 | 10/1958 | Vagenius | 424/76.1 |
| 3,124,459 | 3/1964 | Erwin | 424/76.1 |
| 3,124,460 | 3/1964 | Erwin | 424/76.1 |
| 3,172,817 | 3/1965 | Leupold | 424/76.1 |
| 4,447,243 | 5/1984 | Claiborne | 424/76.1 |
| 4,511,552 | 4/1985 | Cox | 424/76.7 |
| 4,719,105 | 1/1988 | Schleppnik | 424/76.4 |
| 4,906,462 | 3/1990 | Miki et al. | 424/76.1 |

FOREIGN PATENT DOCUMENTS

| 238865 | 10/1988 | Japan . |
| 64-40055 | 2/1989 | Japan . |
| 1124460 | 5/1989 | Japan . |

OTHER PUBLICATIONS

Lange, "Handbook of Chemistry", pp. 830–832, Tenth Edition (1967).

*Primary Examiner*—Patrick J. Ryan
*Attorney, Agent, or Firm*—Sherman and Shalloway

[57] ABSTRACT

A deodorant composition comprising (A) an acidic phosphoric acid compound and (B) a copper compound and as desired, (C) a reducing agent, and a deodorant composite material comprising a substrate and the deodorant composition included therein.

15 Claims, No Drawings

DEODORANT COMPOSITION AND DEODORANT COMPOSITE MATERIAL

This is a division of application Ser. No. 07/118,884, filed Nov. 10, 1987, now U.S. Pat. No. 4,906,462.

This invention relates to a deodorant composition and a deodorant composite material. More specifically, this invention relates to a deodorant composition having deodorant, germicidal and fungicidal properties, and a deodorant composite material comprising a substrate and the deodorant composition included therein.

Inorganic acids, sulfuric acid salts, phosphoric acid salts and organic acids have previously been known as deodorants effective against ammonia and amines. Of these, the phosphates have excellent storage stability and thermal stability, and when they are used in the form of a solution, no precipitate is formed during deodorizing of alkaline substances such as ammonia. In spite of such advantages, these substances have an inferior ability to deodorize mercaptan and the like.

The present inventors have extensively worked in order to solve the above problem, and have now found that the combined use of an acidic phosphoric acid compound and a copper compound exhibits excellent deodorizing activity not only on amines but also on mercaptans; that a composition comprising these compounds in combination has excellent storage stability; and that when they are used further in combination with a reducing agent, their deodorizing activity is further improved.

Thus, the present invention provides a deodorant composition comprising (A) an acidic phosphoric acid compound and (B) a copper compound, and as desired, (C) a reducing agent, and a deodorant composite material comprising a substrate and the deodorant composition included therein The acidic phosphoric acid compound used as component (A) in this invention may be any phosphoric acid having acidity, for example phosphoric acids, acidic phosphoric acid salts and acidic phosphoric acid esters. They may be used either singly or in combination.

Specific examples of the phosphoric acids are phosphoric acid, pyrophosphoric acid, metaphosphoric acid, phosphorous acid, hypophosphorous acid, hydroxyethylidene-1,1-diphosphonic acid, aminotrimethylenephosphonic acid and ethylenediaminetetramethylenephosphonic acid.

Specific examples of the acidic phosphoric acid salts are dihydrogen phosphates, monohydrogen phosphates, acid pyrophosphates, acid metaphosphates, phosphites and hypophosphites. The metal moiety of these salts may, for example, be sodium, potassium, calcium, aluminum, zinc or ammonium. Water-soluble salts are preferred.

Examples of the acidic phosphoric acid esters include compounds of the formula

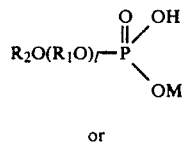

or

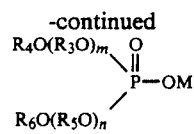

wherein $R_1$, $R_3$ and $R_5$ represents a linear or branched lower alkylene group, $R_2$, $R_4$ and $R_6$ represent an alkyl or alkaryl group having 1 to 30 carbon atoms, M represents hydrogen, a monovalent metal, an ammonium group or an organic ammonium group, and l, m and n each represent an integer of 0 to 20.

Specific examples are acidic monophosphates such as methyl acid phosphate, ethyl acid phosphate, n-propyl acid phosphate, isopropyl acid phosphate, n-butyl acid phosphate, 2-ethylhexyl acid phosphate, isodecyl acid phosphate, tri-n-decyl acid phosphate, lauryl acid phosphate and stearyl acid phosphate; acidic diphosphates such as dibutyl acid phosphate and di-n-octyl acid phosphate; and acidic monophosphates and diphosphates of polyalkylene oxide adducts of higher alcohols or alkylphenols.

The copper compound used as component (B) in this invention may be an inorganic acid salts, organic acid salt, complex or oxide of copper. Specific examples include copper sulfate, copper nitrate, cuprous chloride, cupric chloride, cuprous bromide, cupric bromide, cuprous iodide, copper carbonate, cupric hydroxide, cupric sulfide, copper cyanide, copper acetate, cupric citrate, copper gluconate, copper malate, copper glyoxylate, copper 2-ketoglutarate, copper pyruvate, copper oxaloacetate, copper acid phosphate, acid phosphoric ester copper salt, copper pyrophosphate, copper chlorophyll, sodium copper chlorophyllin, potassium copper chlorophyllin, copper phthalocyanine, copper porphyrin, cuprous oxide and cupric oxide. The inorganic acid salts are preferred in view of cost and availability, and the complexes are preferred in view of safety.

These copper compounds may be used singly or in combination.

It should be understood that when the copper compound is a copper salt of the acidic phosphoric acid compound, it acts concurrently as components (A) and (B).

The use of the reducing agent (C) with the acidic phosphoric acid compound (A) and the copper compound (B) can further improve the deodorizing ability of the resulting composition, and the amount of the components (A) and (B) can be decreased in obtaining the same deodorizing ability.

The reducing agent as component (C) may be any compound having reducing ability. Specific examples are ene-diol compounds such as L-ascorbic acid, sodium L-ascorbate, L-ascorbyl stearates, erythorbic acid, sodium erythorbate and dihydroxyfumaric acid; aldehyde compounds having an aldehyde group in the molecule such as formaldehyde, acetaldehyde, glyoxylic acid, malonaldehyde acid, succinaldehyde acid and aldehyde starch; and inorganic reducing agents such as sodium sulfite and sodium thiosulfate.

As required, the composition of this invention may contain a solvent. The solvent may be properly selected from water and organic acids which can dissolve or disperse the deodorant composition comprising the components (A) and (B) or the deodorant composition comprising the components (A), (B) and (C).

The proportions of the components (A), (B) and (C) in this invention may be properly selected depending upon the properties required of the final composition. Usually, 0.001 to 200 parts by weight, preferably 0.002 to 50 parts by weight, more preferably 0.005 to 20 parts by weight, of the component (B) is used per 100 parts by weight of the component (A). If the amount of the component (B) is too small, the resulting composition may have inferior deodorizing activity. If it is too large, the resulting composition may be undesirable because of the toxicity problem. The amount of the component (C) is usually 0.001 to 50 parts by weight, preferably 0.002 to 10 parts by weight, more preferably 0.005 to 5 parts by weight, per 100 parts by weight of the compound (A).

The deodorant composition of this invention may further contain one or more of conventional deodorants, adsorbents, germicides and fungicidal agents, and various additives such as pigments, coloring agents, stabilizers, antioxidants and dispersants.

The method of preparing the deodorant composition position of this invention is not particularly limited. For example, it may be prepared by dissolving the components uniformly in a solvent to obtain a solution; or by lyophilizing or spray-drying the resulting solution to obtain a dry mixture, or by uniformly mixing the components to obtain a dry mixture.

The deodorant composition of this invention is offered for various applications in the form of an aqueous solution, an organic solvent solution, an aqueous dispersion, a powder, a tablet, etc., or as included in various substrates.

The deodorant composite material of this invention can be obtained by including the deodorant composition comprising (A) the acidic phosphoric acid compound and (B) the copper compound and as desired, (C) the reducing agent in a fiber, a resin, an inorganic material, or a shaped article prepared therefrom.

The type of the fiber used in this invention is not particularly restricted, and may be any of natural, regenerated, synthetic and semisynthetic fibers. Specific examples include cellulosic fibers such as cotton, flax, rayon and pulp; proteinous fibers such as wool and silk; and synthetic fibers such as polyester fibers, polyamide fibers, polyacrylic fibers, Poval fibers, polyolefin fibers, polyurethane fibers and polyvinyl chloride fibers. Inorganic fibers such as glass fibers, metallic fibers, carbon fibers, fibrous activated carbon and asbestos fibers may also be used. The length and diameter of these fibers are not limited. These fibers may be used singly or in combination.

There is no particular restriction on the resin used in this invention, and it may be a thermoplastic or thermosetting resin. Thermoplastic resins shapable into films or sheets are preferred. Specific examples include polyolefins such as polyethylene, polypropylene and polybutadiene; polyvinyl compounds such as polyvinyl alcohol, polyvinyl chloride, polyvinylidene chloride, polystyrene, acrylonitrile/butadiene/styrene copolymer, vinyl chloride/vinyl acetate copolymer and ethylene/vinyl acetate copolymers; cellulose esters such as cellulose diacetate; regenerated cellulose; polyesters; polyamides; and fluorine-containing resins.

The inorganic material used in this invention may be any inorganic material on which the composition of this invention comprising the components (A) and (B) and optionally the component (C) can be carried. Specific examples include activated carbon, alumina, silica gel, zeolite, clay, bentonite, diatomaceous earth and acid clay.

The shaped article prepared from the fiber, resin or inorganic material in this invention is obtained by shaping such a material by various known methods such as knitting, weaving, melt-bonding, extrusion, compression molding, calendering, and injection molding.

The form of the fiber, resin or inorganic material into which the deodorant composition is to be included in this invention is not particularly limited, and it may be in the form of, for example, a powder, particles, needles or fibers. The form of the shaped article is neither limited in particular, and it may, for example, be a sheet, film, paper, woven fabric, nonwoven fabric or foam.

There is no particular limitation on the method of including the deodorant composition of this invention into a shaped article. For example, it can be achieved by immersing the fiber, resin or inorganic material or the shaped article thereof in a solution or aqueous dispersion of the deodorant composition; spraying or coating a solution or aqueous dispersion of the deodorant composition on the fiber, resin or inorganic material or the shaped article thereof; or kneading the deodorant composition with the fiber, resin or inorganic material or the shaped article thereof. Two or more of these methods may be used in combination. A binder may be used in these methods. The type of the binder is not particularly limited, but it is preferably a latex of a polymer containing carboxyl groups or sulfonic acid groups.

The form of the deodorant composite material of this invention is not particularly limited. For example, it may be in the form of a powder, particles, needles or fibers. Alternatively, the composite material in such a form may be processed into a sheet, film, paper, woven fabric, non-woven fabric or foam.

If required, the fiber, resin or inorganic material or the shaped article thereof may be processed simultaneously with the inclusion of the deodorant composition into such a material.

The amount of the deodorant composition of this invention to be included into the fiber, resin or inorganic material or the shaped article thereof varies depending upon the purpose for which the final product is used. Usually, it is 0.5 to 30 %, preferably 1.0 to 20 %, based on the weight of the fiber, resin or inorganic material or the shaped article thereof. If its amount is too small, the resulting composite material might have an insufficient function. If, on the other hand, it is too large, economic disadvantage may result.

When the substrate of the deodorant composite material is a nonwoven fabric, the amount of the deodorant composition included is usually 0.5 to 500 parts by weight per 100 parts of the fibers constituting the nonwoven fabric. If amount is too small, the composite material may have an inferior deodorizing effect. If it is too large, it may impair the feel of the nonwoven fabric and is also economically disadvantageous As required, various additives such as stabilizers, lubricants, fillers, antioxidants, ultraviolet absorbers, processing aids, defoamers, pigments, fire retardants and impact-resistant aids may be added to the deodorant composite material of this invention in amounts which do not degrade the function of the composite material.

Other deodorants adsorbents, germicides, antiseptics or fungicides may be used in combination with the deodorant composite material of this invention if their amounts do not impair the effect of the invention.

Thus, according to this invention, there can be obtained a novel deodorant composition having excellent storage stability and thermal stability and excellent ability to deodorize ammonia, mercaptan and other malodorous substances and being useful as a deodorant, a germicide, a fungicide or the like. By combining this composition with a fiber, resin or inorganic material or a shaped article thereof, a deodorant composite material can be obtained which is in the form of, for example, a filter, a foam, a film, a sheet, a fiber, a woven fabric, a nonwoven fabric or a resin article and can find extensive application.

The following Examples and Comparative Examples illustrate the present invention more specifically. All parts and percentages in these examples are by weight unless otherwise specified.

EXAMPLE 1

In each run, component (A) and component (B) were dissolved in distilled water to prepare 20 g of an aqueous solution. The types and amounts of the components (A) and (B) are shown in Table 1-a.

A 500 mg portion of the resulting aqueous solution was put in a 100 ml Erlenmeyer flask and the flask was stopped. Then, 1 ml of ethylmercaptan (0.5 g/3 liter $N_2$) was added. Thirty minutes later, the amount of ethylmercaptan in the vapor phase was measured by gas chromatography, and the ratio of deodorized ethylmercaptan was calculated.

Separately, a 100 mg portion of the resulting aqueous solution was put in a 100 ml Erlenmeyer flask, and the flask was stopped. Then, 50 microliters of a 2.8% aqueous solution of ammonia was added. Thirty minutes later, the appearance of the solution was observed, and the amount of ammonia in the vapor phase was measured by gas chromatography. Furthermore, the ratio of deodorized ammonia was calculated.

Further, the aqueous solution was put in a 50 ml beaker, and after a glass plate was placed on the beaker, allowed to stand for 20 days. The color of the aqueous solution and the state of precipitate formation were observed.

The results are shown in Table 1-b.

TABLE 1-a

| Run No. | Type of component (A) (used in an amount of 1,000 mg) | Amount of component (B) (copper sulfate pentahydrate) |
|---|---|---|
| Invention | | |
| 1 | sodium acid pyrophosphate | 500 |
| 2 | sodium acid pyrophosphate | 100 |
| 3 | sodium acid pyrophosphate | 50 |
| 4 | sodium acid pyrophosphate | 10 |
| 5 | sodium acid pyrophosphate | 1 |
| 6 | potassium dihydrogen phosphate | 50 |
| 7 | potassium monohydrogen phosphate | 50 |
| 8 | sodium acid meta-phosphate | 50 |
| 9 | hydroxyethylidene-1,1-diphosphonic acid | 50 |
| 10 | phosphorous acid | 50 |
| 11 | hypophosphorous acid | 50 |
| Comparison | | |
| 12 | sodium acid pyrophosphate | not used |
| 13 | aluminum sulfate | not used |
| 14 | ferrous sulfate/ L-ascorbic acid (*) | not used |
| 15 | citric acid | not used |

(*) A mixture of ferrous sulfate ($FeSO_4.7H_2O$) and L-ascorbic acid in a mole ratio of 1:0.05.

TABLE 1-b

| Run No. | Ratio of deodorization (%) $C_2H_5SH$ | Ratio of deodorization (%) $NH_3$ | Appearance observed 30 minutes after $NH_3$ deodorization | Change in appearance with time immediately after mixing | Change in appearance with time 20 days later |
|---|---|---|---|---|---|
| Invention | | | | | |
| 1 | 100 | 100 | no change | pale blue, transparent | pale blue, transparent |
| 2 | 100 | 100 | no change | pale blue, transparent | pale blue, transparent |
| 3 | 99 | 100 | no change | pale blue, transparent | pale blue, transparent |
| 4 | 93 | 100 | no change | pale blue, transparent | pale blue, transparent |
| 5 | 50 | 100 | no change | pale blue, transparent | pale blue, transparent |
| 6 | 100 | 100 | no change | pale blue, transparent | pale blue, transparent |
| 7 | 100 | 100 | no change | pale blue, transparent | pale blue, transparent |
| 8 | 98 | 100 | no change | pale blue, transparent | pale blue, transparent |
| 9 | 100 | 100 | no change | pale blue, transparent | pale blue, transparent |
| 10 | 100 | 100 | no change | pale blue, transparent | pale blue, transparent |
| 11 | 100 | 100 | no change | pale blue, transparent | pale blue, transparent |
| Comparison | | | | | |
| 12 | 0 | 100 | no change | pale blue, transparent | pale blue, transparent |
| 13 | 3 | 100 | white precipitate | colorless transparent | colorless transparent |

TABLE 1-b-continued

| Run No. | Ratio of deodorization (%) $C_2H_5SH$ | $NH_3$ | Appearance observed 30 minutes after $NH_3$ deodorization | Change in appearance with time immediately after mixing | 20 days later |
| --- | --- | --- | --- | --- | --- |
| 14 | 3 | 100 | blackish gray precipitate | blue transparent | brown transparent |
| 15 | 4 | 100 | no change | colorless transparent | pale green |

The results given in Table 1-b demonstrate that the compositions of the invention (Runs Nos. 1 to 11) have better deodorizing activity on mercaptan and ammonia and better stability than the comparative compositions (Runs Nos. 12 to 15).

EXAMPLE 2

In each run, component (A) and component (B) were uniformly mixed and pulverized in a mortar to prepare a sample powder. The types and amounts of the components (A) and (B) are shown in Table 2. A 100 mg portion of the sample powder was put in a 100 ml Erlenmeyer flask, and the flask was stopped. Then, 1 ml of ethylmercaptan (0.5 g/3 liter $N_2$) was added. Sixty minutes later, the amount of ethylmercaptan in the vapor phase was measured by gas chromatography, and the ratio of deodorized mercaptan was calculated.

Separately, a 50 mg portion of the sample powder was put in a 100 ml Erlenmeyer flask, and the flask was stopped. Then, 100 microliters of a 2.8 % aqueous solution of ammonia was added. Thirty minutes later, the amount of ammonia in the vapor phase was measured by gas chromatography, and the ratio of deodorized ammonia was calculated.

The results are shown in Table 2.

TABLE 2

| Run No. | Component (A) | Component (B) | A/B weight ratio | Ratio of deodorization (%) ethyl mercaptan | $NH_3$ |
| --- | --- | --- | --- | --- | --- |
| Invention | | | | | |
| 1 | sodium acid pyrophosphate | copper sulfate pentahydrate | 10/5 | 100 | 100 |
| 2 | sodium acid pyrophosphate | copper sulfate pentahydrate | 10/1 | 98 | 100 |
| 3 | sodium acid pyrophosphate | copper sulfate pentahydrate | 10/0.1 | 86 | 100 |
| 4 | calcium acid pyrophosphate | copper sulfate pentahydrate | 10/1 | 96 | 88 |
| 5 | aluminum dihydrogen tripolyphosphate | copper sulfate pentahydrate | 10/1 | 95 | 90 |
| Comparison | | | | | |
| 6 | aluminum sulfate | none | — | 3 | 100 |
| 7 | ferrous sulfate | none | — | 3 | 100 |
| 8 | citric acid | none | — | 3 | 100 |

It is seen from Table 2 that the compositions of the invention (Runs Nos. 1 to 5) in powder form also have better deodorizing activity than the comparative compositions (Runs Nos. 6 to 8).

EXAMPLE 3

In each run, predetermined amounts of component (A) and component (B) indicated in Table 3 were weighed. For preparation of a powdery composition, they were uniformly mixed, and for preparation of a solution, they were dissolved in a solvent to prepare 20 g of a solution. (Runs Nos. 1 to 8).

A predetermined amount (0.1 g for the powder and 1 g for the solution) of the deodorant composition was taken into a 100 ml Erlenmeyer flask. Furthermore, 1 ml of nitrogen gas containing methylmercaptan in an amount of 20 mg per liter was added, and the flask was stopped. After standing for 1 hour, the amount of methylmercaptan in the vapor phase was measured by gas chromatography, and the ratio of deodorized mercaptan was calculated. The results are shown in Table 3.

For comparison, a sample was prepared in the same way as above except that either one of the components (A) and (B) was not used, and the same methylmercaptan deodorizing test as above was conducted and the ratio of deodorized methylmercaptan was calculated. (Runs Nos. 9 to 13).

As another comparison, the same deodorizing test as above was conducted on ferrous sulfate/L-ascorbic acid and citric acid which are known deodorants, either alone or in combination with a copper compound, and the ratio of deodorized methylmercaptan was calculated (Runs Nos. 14 to 17). The results are also shown in Table 3.

Furthermore, the same deodorizing test as above was carried out except that the amount of the sample taken into the 100 ml Erlenmeyer flask was decreased to 1/10, 70 mg of ammonia was used instead of 20 mg of methylmercaptan, and the standing time was changed to 30 minutes. The ratio of deodorized ammonia was calculated similarly. (Runs Nos. 1 to 17). The results are also shown in Table 3.

TABLE 3

| Run No. | Component (A) Type | Amount (mg) | Component (B) Type | Amount (mg) | Solvent | Ratio of deodorization (%) CH$_3$SH | NH$_3$ |
| --- | --- | --- | --- | --- | --- | --- | --- |
| Invention | | | | | | | |
| 1 | aromatic acid phosphate (*1) | 1000 | copper sulfate.5H$_2$O | 500 | water | 100 | 100 |
| 2 | aromatic acid phosphate (*1) | " | copper sulfate · 5H$_2$O | 50 | water | 100 | 100 |
| 3 | aromatic acid phosphate (*1) | " | copper sulfate · 5H$_2$O | 1 | water | 85 | 100 |
| 4 | aromatic acid phosphate (*1) | " | copper oleate | 50 | none | 100 | 100 |
| 5 | aromatic acid phospahte (*1) | " | sodium Cu chlorophyllin | 50 | water | 98 | 100 |
| 6 | aliphatic acid phosphate (*2) | 1000 | copper naphthenate | 50 | none | 100 | 100 |
| 7 | aliphatic acid phosphate (*2) | " | copper naphthenate | 50 | toluene | 100 | 100 |
| 8 | methyl acid phosphate (*3) | " | copper sulfate.5H$_2$O | 50 | water | 100 | 100 |
| Comparison | | | | | | | |
| 9 | aromatic acid phosphate (*1) | 1000 | none | — | water | 0 | 100 |
| 10 | aliphatic acid phosphate (*2) | " | none | — | none | 0 | 100 |
| 11 | methyl acid phosphate (*3) | " | none | — | water | 1 | 100 |
| 12 | none | — | copper sulfate.5H$_2$O | 50 | water | 100 | 22 |
| 13 | none | — | Copper oleate | 50 | toluene | 100 | 3 |
| 14 | ferrous sulfate/L-ascorbic acid (*4) | 1000 | none | — | water | 5 | 100 |
| 15 | ferrous sulfate/L-ascorbic acid (*4) | " | copper sulfate.5H$_2$O | 50 | water | 80 | 100 |
| 16 | citric acid | " | none | — | water | 2 | 100 |
| 17 | citric acid | " | copper sulfate.5H$_2$O | 50 | water | 30 | 100 |

(*1) GAFAC-RE-610 (acid phosphate of alkylphenol-polyethylene oxide adduct, a product of Toho Chemical Co., Ltd.)
(*2) GAFAC-RL-210 (acid phosphate of higher alcohol-polyethylene oxide adduct, a product of Toho Chemical Co., Ltd.)
(*3) AP-1 (produced by Daihachi Chemical Industry Co., Ltd.)
(*4) A mixture of ferrous sulfate (FeSO$_4$.7H$_2$O) and L-ascorbic acid in a mole ratio of 1:0.05

The results given in Table 3 show that the deodorant compositions of this invention (Runs Nos. 1 to 8) have better deodorizing activity on ammonia and mercaptan than the comparative compositions (Runs Nos. 9 to 17).

EXAMPLE 4

The various deodorants or deodorant compositions prepared in Example 3 were left to stand in ampoules for 1 week, and then subjected to the same tests as in Example 3. Much the same results as in Example 3 were obtained except that an aqueous solution of a deodorant composition composed of ferrous sulfate, L-ascorbic acid and copper sulfate pentahydrate turned brown, and the ratio of deodorized mercaptan decreased to 35 %.

It is seen from this that the deodorant composition of this invention has excellent storage stability.

EXAMPLE 5

In each run, predetermined amounts of component (A), component (B) and component (C) indicated in Table 4 were weighed. For preparation of a powdery composition, they were uniformly mixed, and for preparation of a solution, they were dissolved in a solvent to prepare 400 g of a solution. (Runs Nos. 1 to 14).

A predetermined amount (0.1 g for the powder and 1 g for the solution) of the deodorant composition was taken into a 100 ml Erlenmeyer flask. Furthermore, 1 ml of nitrogen gas containing methylmercaptan in an amount of 200 mg per liter was added, and the flask was stopped. After standing for 1 hour, the amount of methylmercaptan in the vapor phase was measured by gas chromatography, and the ratio of deodorized methylmercaptan was calculated. The results are shown in Table 4.

For comparison, a sample was prepared in the same way as above except that either one of the components (A) and (B) was not used, and the same methylmercaptan deodorizing test as above was conducted and the ratio of deodorized methylmercaptan was calculated. (Runs Nos. 15 to 19).

Furthermore, the same deodorizing test as above was carried out except that 70 mg of ammonia was used instead of 200 mg of methylmercaptan, and the standing time was changed to 30 minutes. The ratio of deodorized ammonia was calculated similarly. (Runs Nos. 1 to 19). The results are also shown in Table 4.

TABLE 4

| Run No. | Component (A) Type | Amount (mg) | Component (B) Type | Amount (mg) | Component (C) Type | Amount (mg) | Solvent | Ratio of deodorized CH$_3$SH measured one hour later | Ratio of deodorized NH$_3$ measured 30 minutes later |
| --- | --- | --- | --- | --- | --- | --- | --- | --- | --- |
| Invention | | | | | | | | | |
| 1 | Sodium acid pyrophoshate | 10000 | Copper sulfate pentahydrate | 10 | L-ascorbic acid | 1 | water | 94 | 100 |
| 2 | Sodium acid pyrophosphate | 10000 | Copper sulfate pentahydrate | 10 | L-ascorbic acid | 10 | water | 100 | 100 |
| 3 | Sodium acid pyrophosphate | 10000 | Copper sulfate pentahydrate | 10 | L-ascorbic acid | 100 | water | 100 | 100 |
| 4 | Sodium acid pyrophosphate | 10000 | Copper sulfate pentahydrate | 10 | L-ascorbic acid | 10 | none | 100 | 100 |
| 5 | Sodium acid pyrophosphate | 10000 | Copper sulfate pentahydrate | 10 | dihydroxyfumaric acid | 10 | water | 100 | 100 |
| 6 | Sodium acid | 10000 | Copper sulfate | 10 | glyoxylic acid | 10 | water | 100 | 100 |

TABLE 4-continued

| Run No. | Component (A) Type | Component (A) Amount (mg) | Component (B) Type | Component (B) Amount (mg) | Component (C) Type | Component (C) Amount (mg) | Solvent | Ratio of deodorized CH₃SH measured one hour later | Ratio of deodorized NH₃ measured 30 minutes later |
|---|---|---|---|---|---|---|---|---|---|
| | pyrophosphate | | pentahydrate | | | | | | |
| 7 | Sodium acid pyrophosphate | 10000 | Copper sulfate pentahydrate | 10 | sodium sulfite | 10 | water | 100 | 100 |
| 8 | phosphoric acid | 10000 | copper sulfate pentahydrate | 10 | L-ascorbic acid | 10 | water | 100 | 100 |
| 9 | phosphorous acid | 10000 | copper sulfate pentahydrate | 10 | L-ascorbic acid | 10 | water | 100 | 100 |
| 10 | acid phosphate* | 10000 | copper sulfate pentahydrate | 1 | L-ascorbic acid | 10 | water | 96 | 10 |
| 11 | acid phosphate* | 10000 | copper sulfate pentahydrate | 10 | L-ascorbic acid | 10 | water | 100 | 100 |
| 12 | acid phosphate* | 10000 | anhydrous cupric chloride | 10 | L-ascorbic acid | 10 | water | 100 | 100 |
| 13 | acid phosphate* | 10000 | sodium copper chlorophyllin | 10 | L-ascorbic acid | 10 | water | 98 | 100 |
| 14 | sodium acid pyrophosphate | 10000 | copper sulfate pentahydrate | 10 | none | — | water | 41 | 100 |
| Comparison | | | | | | | | | |
| 15 | sodium acid pyrophoshate | 10000 | none | — | none | — | water | 0 | 100 |
| 16 | none | — | copper sulfate pentahydrate | 10 | none | — | water | 38 | 10 |
| 17 | none | — | none | — | L-ascorbic acid | 10 | water | 1 | 1 |
| 18 | none | — | copper sulfate pentahydrate | 10 | L-ascorbic acid | 10 | water | 1 | 3 |
| 19 | sodium acid pyrophosphate | 10000 | none | — | L-ascorbic acid | 10 | water | 1 | 100 |

*GAFA-C.RE-610 (See the footnote to Table 3)

The results given in Table 4 show that the deodorant composition comprising the acidic phosphoric acid compound (A), the copper compound (B) and the reducing agent (C) show an equivalent deodorizing effect to the deodorizing composition composed only of the components (A) and (B) even when the amount of the copper compound (B) is small.

EXAMPLE 6

Water was added to 100 parts of the same aromatic acidic phosphate as used in Example 3 and 10 parts of copper sulfate pentahydrate to prepare a 10% aqueous solution.

The aqueous solution was impregnated in granular activated carbon (average particle diameter 5 mm, made by Kokusan Kagaku K. K.) using Poval as a binder. The impregnated activated carbon was dried at 120° C. for 2 hours to obtain a granular carbon (1) having the deodorant composition carried thereon in a proportion of 10%.

EXAMPLE 7

Copper oleate (0.1 part) was added to 2.46 parts of the same aliphatic acidic phosphate as used in Example 3 and they were well mixed in a mortar. The resulting mixture was mixed with 100 parts of polyethylene resin (Showlex 720FS, low-density polyethylene produced by Showa Denko Co., Ltd.) in a Henschel mixer to obtain a resin composition comprising the deodorant composition. The resin composition was extruded and stretched to form a biaxially stretched film (2) having a thickness of 0.1 mm.

EXAMPLE 8

One part of copper oleate was added to 100 parts of the same aromatic acidic phosphate as used in Example 3, and the mixture was heated to form a liquid deodorant composition. Two parts of the liquid composition was mixed with 100 parts of polyol (GR 3000, a product of Sanyo Chemical Co., Ltd.). The resulting mixture was mixed with a solution composed of 42 parts of tolylene diisocyanate (a mixture of 80% of 2,4-tolylene diisocyanate and 20% of 2,6-tolylene diisocynate; NCO index=105), 3.2 parts of water, 0.3 part of tin octenoate, 0.2 part of triethylenediamine and 1.5 parts of silicone oil by a mixer. The mixture was reacted and foamed in a customary manner to obtain a urethan (polyurethane) foam (3) containing the deodorant composition.

EXAMPLE 9

A random web having a basis weight of 100 g/m² from polyester fibers with a size of 4.5 denier by using a webber. An aqueous solution composed of 100 parts of the 10% aqueous solution prepared in Example 6 and 60 parts of a latex of carboxyl-modified styrene/ butadiene copolymer was sprayed onto the web, and dried to give a non-woven fabric (4) containing the deodorant composition at a rate of 25 g/m².

EXAMPLE 10

A terpolymer (98 parts) composed of 91.2% of acrylonitrile, 8.0% of methyl acrylate and 0.8% of sodium methallylsulfonate, 1.95 parts of the same aliphatic acidic phosphate as used in Example 3 and 0.05 part of copper oleate were dissolved in dimethylformamide to prepare a 20% solution. This solution was spun into a 50% aqueous solution of dimethylformamide at 20° C., and then subjected to customary steps of drawing, washing with water, drying and relaxing heat-treatment to form acrylic synthetic fibers (5).

EXAMPLE 11 (Deodorizing Test)

One gram of each of the deodorant composite materials obtained in Examples 6 to 10 was tested for deodorizing activity in the same way as in Example 3. The results are shown in Table 5.

TABLE 5

| Type of the deodorant composite material | Ratio of deodorized methylmercaptan (%) | Ratio of deodorized ammonia (%) |
|---|---|---|
| Granular material (1) | 100 | 100 |
| Film (2) | 98 | 100 |
| Urethan foam (3) | 99 | 100 |
| Nonwoven fabric (4) | 100 | 100 |
| Synthetic fibers (5) | 98 | 100 |

It is seen from the results shown in Table 5 that the deodorant composite materials of this invention have excellent deodorizing activity on ammonia and mercaptan.

REFERENTIAL EXAMPLE 1

A random web having a basis weight of 100 g/m² was produced from viscose rayon fibers with a size of 4.5 denier by using a webber. An aqueous solution having a solids concentration of 10% composed of 100 parts of acidic sodium pyrophosphate, 1 part of copper sulfate, 200 parts of carboxyl-modified styrene/butadiene latex (LX415A, TS=43%, made by Nippon Zeon Co., Ltd.) and water was sprayed onto the web and then dried. The spraying and drying were repeated to give nonwoven fabrics (I) to (III) containing the deodorant composition in the amounts shown in Table 6.

REFERENTIAL EXAMPLE 2

A spun-bond type nonwoven fabric having a basis weight of 50 g/m² composed of polyester fibers with a size of 2.5 denier was impregnated with an aqueous solution having a solids concentration of 10% and composed of 150 parts of acidic sodium pyrophosphate, 1 part of copper sulfate, 300 parts of carboxyl-modified butadiene/latex (LX415A; TS=43%; a product of Nippon Zeon Co., Ltd.) and water. The excess of the aqueous solution was removed by a squeeze roll so as to provide the desired pick-up. The impregnated nonwoven fabric was dried to give a nonwoven fabric (IV) containing the deodorant composition at a rate of 50 g/m².

REFERENTIAL EXAMPLE 3

A nonwoven fabric (V) containing the deodorant composition at a rate of 50 g/m² was obtained in the same way as in Referential Example 2 except that 5 parts of copper chlorophyllin sodium was used instead of 1 par of copper sulfate, the amount of acidic sodium pyrophosphate was changed to 100 parts, and 10 parts of powdery activated carbon was additionally used.

REFERENTIAL EXAMPLE 4

A nonwoven fabric (VI) containing the deodorant composition at a rate of 10 g/m² was obtained in the same way as in Referential Example 1 except that 100 parts of ferrous sulfate/L-ascorbic acid mixture (1:0.05 by mole) was used instead of 100 parts of the sodium acid pyrophosphate.

EXAMPLE 12

One gram of each of the nonwoven fabrics (I) to (VI) obtained in Referential Examples 1 to 4 was put in a 100 ml Erlenmeyer flask filled with air containing 0.7 mg of ammonia. One hour later, the concentration of ammonia in the vapor phase was measured by gas chromatography, and the ratio of deodorized ammonia was calculated. The results are shown in the column headed "1st time".

EXAMPLE 13

To examine the duration of ammonia deodorizing activity, each of the nonwoven fabrics used in Example 12 was again subjected to the operation of Example 12, and the ratio of deodorized ammonia was calculated (2nd time). Each of the used nonwoven fabrics was again subjected to the same operation, and the ratio of deodorized ammonia was calculated (3rd time). The results are shown in Table 6 under the headlines "2nd time" and "3rd time", respectively.

TABLE 6

| Run No. | Nonwoven fabric | Amount of the deodorant composition carried (g/m²) | Appearance of the nonwoven fabric | Ratio of deodorized ammonia | | |
|---|---|---|---|---|---|---|
| | | | | 1st time | 2nd time | 3rd time |
| Invention | | | | | | |
| 1 | (I) | 10 | white | 92 | 83 | 65 |
| 2 | (II) | 100 | white | 100 | 100 | 94 |
| 3 | (III) | 400 | white | 100 | 100 | 100 |
| 4 | (IV) | 50 | white | 100 | 100 | 99 |
| 5 | (V) | 50 | gray | 100 | 100 | 97 |
| Comparison | | | | | | |
| 6 | (VI) | 10 | pale brown | 36 | 9 | 0 |

It is seen from Table 6 that the deodorant composite materials of this invention have excellent ammonia deodorizing activity with excellent duration.

EXAMPLE 14

One gram of each of the nonwoven fabrics (I) to (VI) obtained in Referential Examples 1 to 4 was put in a 100 ml Erlenmeyer flask filled with air containing 0.02 mg of methylmercaptan, and the flask was stopped. One hour later, the concentration of methylmercaptan in the vapor phase was measured by gas chromatography, and the ratio of deodorized methylmercaptan was calculated. The results are shown in Table 7 under the headline "1st time".

EXAMPLE 15

To examine the duration of methylmercaptan deodorizing activity, each of the nonwoven fabrics used in Example 14 was again subjected to the operation of Example 14, and the ratio of deodorized methylmercaptan was calculated (2nd time). Each of the used nonwoven fabrics was again subjected to the same operation, and the ratio of deodorized ammonia was calculated (3rd time). The results are shown in Table 7 under the headlines "2nd time" and "3rd time", respectively.

TABLE 7

| Run No. | Nonwoven fabric | Amount of the deodorant composition carried (g/m²) | Ratio of deodorized methylmercaptan | | |
|---|---|---|---|---|---|
| | | | 1st time | 2nd time | 3rd time |
| Invention | | | | | |
| 1 | (I) | 10 | 61 | 53 | 45 |
| 2 | (II) | 100 | 80 | 76 | 70 |
| 3 | (III) | 400 | 100 | 100 | 98 |
| 4 | (IV) | 50 | 75 | 71 | 68 |
| 5 | (V) | 50 | 100 | 100 | 100 |
| Comparison | | | | | |
| 6 | (VI) | 10 | 31 | 24 | 11 |

It is seen from Table 7 that the deodorant composite materials of this invention have excellent methylmercaptan deodorizing activity with excellent duration.

What is claimed is:

1. A deodorant composite material comprising a substrate and included therein, a deodorant composition comprising (A) 100 parts by weight of an acidic phosphoric acid compound selected from the group consisting of phosphoric acids and acidic phosphoric acid esters and (B) 0.01 to 200 parts by weight of a copper compound.

2. A deodorant composite material comprising a substrate and included therein, a deodorant composition comprising (A) 100 parts by weight of an acidic phosphoric acid compound selected from the group consisting of phosphoric acids, phosphoric acid salts and acidic phosphoric acid esters, (B) 0.00to 200 parts by weight of a copper compound and (C) 0.001 to 50 parts by weight of a reducing agent.

3. The composite material of claim 1 or 2 wherein the deodorant composition is included in an amount of 0.5 to 30% based on the weight of the substrate.

4. The composite material of any one of claim 1 or 2 which is in the form of a nonwoven fabric.

5. The composite material of claim 4 wherein the deodorant composition is included in an amount of 0.5 to 500 parts by weight per 100 parts by weight of the fibers constituting the nonwoven fabric.

6. The composite material of any one of claim 1 or 2 which is in the form of a film.

7. The composite material of any one of claims 1 or 2 wherein said substrate comprises a polyurethane foam and said deodorant composition is contained within said foam.

8. The composite material of any one of claim 1 or 2 which is in the form of a fiber.

9. The composite material of any one of claim 1 or 2 which is in the form of a granular material.

10. The deodorant composite material of claim 1 wherein the copper compound is selected from the group consisting of inorganic acid salts, organic acid salts, complexes and oxides of copper.

11. The deodorant composite material of claim 2 wherein the copper compound is selected from the group consisting of inorganic acid salts, organic acid salts, complexes and oxides of copper.

12. The deodorant composite material of claim 2 wherein the reducing agent is selected from the group consisting of ene-diol compounds, aldehyde compounds and inorganic reducing agents.

13. The deodorant composite material of claim 2 wherein the reducing agent is selected from the group consisting of ene-diol compounds, aldehyde compounds and inorganic reducing agents.

14. The composite material of claim 2 wherein the reducing agent of the deodorant composition is selected from the group consisting of L-ascorbic acid, sodium L-ascorbate, L-ascorbyl stearate, erythorbic acid, sodium erythorbate, dihydroxyfumaric acid, formaldehyde, acetaldehyde, glyoxylic acid, malonaldehyde acid, succinaldehyde acid, aldehyde starch, sodium sulfite and sodium thiosulfate.

15. The composite material of claim 2 wherein the reducing agent of the deodorant composition is selected from the group consisting of L-ascorbic acid, sodium L-ascorbate, L-ascorbyl stearate, erythorbic acid, sodium erythorbate, dihydroxyfumaric acid, formaldehyde, acetaldehyde, glyoxylic acid, malonaldehyde acid, succinaldehyde acid, aldehyde starch, sodium sulfite and sodium thiosulfate.

* * * * *